US005336617A

United States Patent [19]

Sugitani et al.

[11] Patent Number: 5,336,617

[45] Date of Patent: Aug. 9, 1994

[54] PROCESS FOR PREPARING TREHALULOSE AND ISOMALTULOSE

[75] Inventors: Toshiaki Sugitani; Kenichiro Tsuyuki, both of Kamakura; Yukie Miyata, Tokyo; Tadashi Ebashi, Nagaregama; Hideaki Okui, Chiba; Yoshikazu Nakajima, Yamato; Kenzo Sawada, Tokyo, all of Japan

[73] Assignees: Mitsui Sugar Co., Ltd., Tokyo, Japan; Suedzucker AG Mannheim/Ochsenfurt, Mannheim, Fed. Rep. of Germany

[21] Appl. No.: 45,128

[22] Filed: Apr. 12, 1993

Related U.S. Application Data

[62] Division of Ser. No. 782,657, Oct. 25, 1991, Pat. No. 5,229,276.

[51] Int. Cl.$^5$ ........................ C12N 1/20; C12P 19/18; C12P 19/04

[52] U.S. Cl. .................................. 435/252.1; 435/95; 435/96; 435/97; 435/99; 435/100; 435/170; 435/252.34; 435/253.3; 435/874

[58] Field of Search ............. 435/252.1, 252.34, 253.3, 435/874, 170, 97; 432/822

[56] References Cited

U.S. PATENT DOCUMENTS

| | | |
|---|---|---|
| 4,225,586 | 9/1980 | Imada et al. ........................ 935/170 |
| 4,356,262 | 10/1982 | Heady . |
| 4,359,531 | 11/1982 | Bucke et al. . |
| 4,423,150 | 12/1983 | Heady . |
| 4,431,733 | 2/1984 | Horwath et al. . |
| 4,670,387 | 6/1987 | Bucke et al. . |
| 4,788,145 | 11/1988 | Munir . |
| 4,857,339 | 8/1989 | Maselli et al. . |
| 4,898,820 | 2/1990 | Hitoshio et al. . |

FOREIGN PATENT DOCUMENTS

| | | |
|---|---|---|
| 0109009 | 5/1984 | European Pat. Off. . |
| 1049800 | 7/1959 | Fed. Rep. of Germany . |
| 57-10720 | 2/1982 | Japan . |
| 58-38156 | 8/1983 | Japan . |
| 60-9797 | 3/1985 | Japan . |
| 2257888 | 10/1990 | Japan . |
| 2273192 | 11/1990 | Japan . |
| 3160995 | 7/1991 | Japan . |

OTHER PUBLICATIONS

Patent Abstracts of Japan, vol. 10, No. 390 (C-394)(2447), Dec. 26, 1986 & JP-A-61 177 995 (Lotte Co. Ltd.) Aug. 9, 1986.

*Primary Examiner*—Herbert J. Lilling
*Attorney, Agent, or Firm*—Wegner, Cantor, Mueller & Player

[57] ABSTRACT

The present invention relates to a process for preparing trehalulose and isomaltulose wherein at least the trehalulose-forming enzyme system of a trehalulose-forming microorganism is contacted with a sucrose solution to convert it into trehalulose and isomaltulose in the weight ratio of at least 4:1.

2 Claims, No Drawings

PROCESS FOR PREPARING TREHALULOSE AND ISOMALTULOSE

This application is a divisional of Ser. No. 07/782,657, filed Oct. 25, 1991, now U.S. Pat. No. 5,229,276.

BACKGROUND OF THE INVENTION

1. Field of the Invention

The present invention relates to a process for preparing trehalulose and isomaltulose. More specifically, the invention relates to the process for preparing a high trehalulose syrup which comprises converting sucrose into trehalulose and isomaltulose using a sugar-conversion enzyme produced by novel microorganisms.

2. Description of the Prior Art

Isomaltulose and trehalulose are found in honey, are taste sweet and are chemically classified as hetero-disaccharides, which are composed of glucose and fructose. These components are linked with an $\alpha$-1,6-glucosidic linkage in isomaltulose, and with an $\alpha$-1,1-glucosidic linkage in trehalulose.

It has been well known that isomaltulose is odontologically non-cariogenic. Recently trehalulose was also demonstrated to have non-caries inducing properties in in vitro and in vivo experiments. These facts promoted a wide use of trehalulose and isomaltulose-containing syrup called "Isomaltulose Syrup".

Trehalulose and isomaltulose are usually formed simultaneously from sucrose through glucosidic transfer catalyzed by $\alpha$-glucosyltransferase found in some specific microorganisms, for example *Protaminobacter rubrum,* Serratia spp. and Erwinia spp. German Patent No. 1049800, published in 1959, firstly described a microbiological process for producing crystalline isomaltulose from sucrose using some specific microorganisms represented by *Protaminobacter rubrum.* Japanese Patent Kokoku No. 58-38156 discloses a continuous aerobic culture process for converting sucrose to isomaltulose using a bacterial strain selected from a group comprising Protaminobacter, Serratia, Erwinia and Leuconostoc. Japanese Patent Kokoku No. 60-9797 also describes a production method of isomaltulose using immobilized enzyme derived from a strain of Erwinia spp. Japanese Patent Kokoku No. 57-10720 discloses a process for preparing isomaltulose which comprises culturing a microorganism belonging to the genus Protaminobacter or Serratia in a sucrose solution under aerobical condition. In these conventional processes, the syrup is produced as a subsidiary product.

In these processes particularly suited to crystalline isomaltulose production, a ratio of trehalulose to isomaltulose in quantity formed from sucrose by enzymic conversion lays in the range of 1:6 to 1:10. After most of isomaltulose is cystallized and centrifuged off from the reaction mixture, the residual matter is obtained in a form of molasses containing trehalulose in a concentration substantially higher than isomaltulose.

Remaining syrup in which crystalline isomaltulose obtained by this conventional method has been recovered contains isomaltulose usually in a concentration near saturation and then isomaltulose is apt to crystallize during its storage, because of having lower solubility of isomaltulose in water. Such phenomena often may cause a lowered commercial value of the product and a difficulty of pumping transportation. In order to avoid such disadvantage, it is necessary to prepare a trehalulose syrup having a concentration of isomaltulose below the saturation point.

Furthermore, all crude isomaltulose solutions obtained in enzymic treatments of sucrose in these conventional processes usually contain considerable amounts of glucose, fructose and isomaltose in addition to larger components of isomaltulose and trehalulose. The presence of glucose and fructose, which represent about 5% of the total saccharide content, causes a considerable reduction of the production efficiency, and moreover shows a heavy color formation during processes operated at higher temperatures for recovering isomaltulose in crystalline forms from the solution. Therefore large capacity decolorization units are required in a conventional isomaltulose production factory, in particular wherein the residual matter is processed into a syrup for use in foodstuff.

Generally the residual matter obtained finally from the process of isomaltulose recovery can be processed into a food grade syrup in a series of procedures composed of decolorization, deionization, filtration and evaporation. The syrup contains all components found originally in the crude isomaltulose solution, while the main component of the syrup is not isomaltulose, but trehalulose.

It is well known that isomaltulose can be used suitably in a variety of foods, particularly in low-cariogenic foods as a sole substitute of sucrose in their conventional formulations.

However it is undesirable that the solubility of isomaltulose in water is considerably lower than that of sucrose. Thus crystalline preparations of isomaltulose has been seldom used in such foods as jams, marmalades, gelatins, youkan (a gelatin-like Japanese sweet food) and other foods which traditionally contain sucrose in a high concentration, because the deteriorative recrystallization of isomaltulose is expected to occur in these foods in storage, when they are prepared by using isomaltulose wholly or partly in place of sucrose in their conventional formulations.

Trehalulose and isomaltulose preparations, in particular high trehalulose syrups, if abundantly available, are considered to be more readily substituted for sucrose in such foods as mentioned above than crystalline isomaltulose, because of the high solubility in water and the preferable sweet taste of trehalulose. Trehalulose rich preparations, as high trehalulose syrups, are therefore required increasingly by food manufacturers, while they are still provided only in limited quantities in the conventional processes.

SUMMARY OF THE INVENTION

The inventors have long been searching such microorganisms as produce trehalulose in a higher yield but monosaccharide in a minimum from sucrose. They discovered recently that novel strains of bacteria could produce mainly trehalulose and subsidiary isomaltulose from sucrose in company with only a minimum by-production of monosaccharide, and that a trehalulose and isomaltulose syrup prepared thereof had a novel composition entirely different from the conventional one, while the both were low-cariogenic as well.

The novel strain mentioned above, named FIX-45 and MX-232 which were isolated from soil samples collected in a sugar processing site in Udronthani, Thailand, have been identified as strains of *Pseudomonas mesoacidophila* and *Agrobacterium radiobacter.* Prior art is totally silent on such Pseudomonas and Agrobacterium species which produce trehalulose and/or isomaltulose from sucrose.

In working this invention, any of the strains of bacteria as the enzyme producer which belong to the genus Pseudomonas and genus Agrobacterium and having properties for converting sucrose to trehalulose and isomaltulose may be used. The strain MX-45 and MX-232 isolated from soil samples mentioned above are merely an example of such strains.

The bacteriological characteristics of MX-45 are as follows:

a) Morphology

Phase microscopic observations and ordinary staining tests have been made for the 3 days culture on nutrient agar slants at 28° C. The cells are rod-shaped, 1.0 μm in width and from 1.6 to 2.6 μm in length. Gram-negative rods without polymorphism. Motile with polar flagella. Non-sporulating.

b) Cultural characteristics on various media (1) Nutrient agar plate: After 3 days culture at 28° C., circular, raised colonies of 1 to 3 mm in diameter with entire margins are formed. The surface is smooth, opaque and gray white.

(2) Nutrient broth: After 3 days culture at 28° C., turbid growth, substantially with a small amount of sedimentation, and a pellicle were observed.

(3) King A, and King B media: During 30 days incubated at 20° C., no fluorescent substance, pyocyanine or carotinoid is produced.

(c) Physiological characteristics:

(1) OF (oxidative-fermentative) test: Oxidative (2) Production of pigment: None (3) Range of growth for temperature: 10° to 38° C.

(4) Cytochrome oxidase: Positive.

(5) Reduction of nitrates: Positive (6) Decarboxylase activity (a) Alginine: Positive (b) Lysine: Negative (c) Ornithine: Negative (7) Denitrification: Negative (8) Liquefaction of gelatin (GEL): Positive (9) Hydrolysis of starch: Negative

(10) Hydrolysis of Tween 80: Negative

(11) Assimilation of carbon sources:

| | |
|---|---|
| D-Glucose | + |
| D-Fructose | + |
| D-Galactose | + |
| L-Arabinose | + |
| D-Xylose | + |
| D-Mannose | + |
| Maltose | + |
| Trehalose | + |
| Sucrose | + |
| Raffinose | + |
| D-Sorbitol | + |
| D-Mannitol | + |
| Lactose | − |

(+: Growth,
-: No growth)

(12) Hydrolysis of esculin: Positive

(13) MR (methyl red) test: Negative

(14) VP (Voges-Proskauer) test: Negative

(15) production of indole: Negative

(16) Utilization of citrate: Positive

(17) Urease: Positive

(18) Catalase: Positive

(19) Production of hydrogen sulfide: Negative

(20) Oxygen demand: Aerobic

Comparison of the above bacteriological characteristics of Strain MX-45 with description in Bergy's Manual of Systematic Bacteriology, Volumn 2, shows that the Strain MX-45 belongs to *Pseudomonas mesoacidophila* which is a strictly aerobic gram-negative rod. Samples of this Strain MX-45 have been deposited with the Fermentation Research institute, Agency of Industrial Science and Technology (FERM), Tsukuba, Japan, and assigned a number of FERM BP808.

The bacteriological characteristics of MX-232 are as follows:

a) Morphology

Phase microscopic observations and ordinary staining tests have been made for 3 days cultures on nutrient agar slants at 28° C. The cells are rod-shaped, 0.8 in diameter and 1.5 to 3.0 m length. Gram-negative, motile with peritrichous flagella. Non-sporulating.

b) Cultural characteristics on various media

Grown at 26° C. and observed for 1 to 14 days.

(1) Nutrient agar plate: After 3–4 days culture at 26° C., circular, raised colonies of 2 to 3 mm diameter with entire margins are formed. The surface is smooth, opaque, gray white.

(2) Nutrient broth: After 3–4 days culture at 26° C. A pellicle appeared, and after a while a part of pellicle sinked to the bottom.

(3) Sucrose containing media: After 3–4 days culture at 26° C., viscosity of medium increase with copious extracellular polysaccharides formation.

c) Physiological characteristics (1) OF (oxidative-fermentative) test: Oxidative.

(2) Production of pigment: None (3) Range of growth for temperature: 10° to 38° C.

(4) Cytochrome oxidase: Positive.

(5) Reduction of nitrates: Positive.

(6) Decarboxylase activity

Alginine: Negative.

Lysine: Negative.

Ornithine: Negative.

(7) Denitrification: Negative.

(8) Liquefaction of gelatin (GEL): Negative.

(9) Hydrolysis of starch: Negative.

(10) Hydrolysis of Tween 80: Negative.

(11) Assimilation of carbon sources:

| | |
|---|---|
| D-Glucose | + |
| D-Fructose | + |
| D-Galactose | + |
| L-Arabinose | + |
| D-Xylose | + |
| D-Mannose | + |
| Maltose | + |
| Trehalose | + |
| Sucrose | + |
| Raffinose | + |
| D-Sorbitole | + |
| D-Mannitole | + |
| Inositole | + |
| Glycerol | + |
| Citric acid | + |
| Acetic acid | − |
| Succinic acid | + |
| 2-keto gluconic acid | ± |
| L-Alanine | + |
| β-Alanine | + |
| Lactose | + |

(+: Growth,
±: Growth weakly,
−: No growth)

(12) Hydrolysis of esculin: Positive.

(13) MR (methyl red) test: Negative.
(14) VP (Voges-Proskauer) test: Negative.
(15) Production of indole: Negative.
(16) Urease: Positive.
(17) Catalase: Positive.
(18) Production of hydrogen sulfide: Negative.
(19) Oxygen demand: Aerobic.
(20) Production of 3-keto lactose: Positive.
(21) DNase test: Negative.
(22) The GC (guanine-cytosine) content of DNA: 59.2 mol %
(23) Phytopathogenicity (Tumors produced on wounded stems): Negative.

Comparison of the above bacteriological characteristics of Strain MX-232 with description in Bergy's Manual of Systematic Bacteriology shows that the Strain MX-232 belongs to *Agrobacterium radiobacter* which is a strictly aerobic gram-negative rod. Samples of this Strain MX-232 have been deposited with the Fermentation Research Institute, Agency of Industrial Science and Technology (FERM), Tsukuba, Japan, and assigned a number of FERM BP3620. It has hitherto not been known that a bacterium belonging to the genus Agrobacterium may convert a sugar into trehalulose and isomaltulose, and hence the use of this strain is also important aspect of the present invention.

It has never been known that the genus Pseudomonas and genus Agrobacterium involve such strains as converting sucrose to isomaltulose and trehalulose. Therefore the employment of strains belonging to the genus Pseudomonas or genus Agrobacterium is an important characteristic of this invention, whereof detailed descriptions are given below.

The enzyme, which is occurred in such strains and active in the conversion of sucrose to trehalulose and isomaltulose, is considered to be a kind of glucosyltransferase. Its production is induced by sucrose, fructose or isomaltulose in the growth medium, and exists in a cell-associated state. Therefore, industrially the cultured bacterial cells can be incorporated wholly in immobilized enzyme particles, which are placed in a column and brought into contact with a sucrose solution passing through the column for converting sucrose to trehalulose and isomaltulose. The resultant crude solution of trehalulose and isomaltulose is deionized, clarified and finally evaporated to a syrup in a desired concentration.

The Pseudomonas or Agrobacterium bacteria are generally highly variable in their characteristics and subjected readily to a natural or artificial mutation. However, one can use any of such mutants and variants for a practice of this invention, as far as it possesses or retains the ability to produce an enzyme activity converting sucrose to trehalulose and isomaltulose.

In the present invention, cultivation of a microorganism employed for enzyme production is carried out under aerobic conditions. As carbon sources of the media, one can use any of those materials as sucrose, affination syrup, waste molasses, glucose, fructose, maltose, glycerol, organic acids and so forth, more preferably sucrose, affination syrup and waste molasses. Content of carbon sources in a medium is ranged from 1 to 15% (w/v), more preferably from 5 to 13% (w/v). As nitrogen sources of the media, one can use any of those organic and inorganic materials as yeast extract, meat extract, peptone, malt extract, corn steep liquor, urea, ammonium sulfate, ammonium nitrate, ammonium chloride, ammonium phosphate and so forth, particularly preferable yeast extract and corn steep liquor. As inorganic salts of the media, one can use any of those salts as generally required for bacterial growth as phosphates, magnesium sulfate, calcium carbonate, potassium chloride, ferrous sulfate and so forth, alone or in a combination thereof. Furthermore one can any other organic or inorganic materials in the media, if required.

Cultivation is carried out at a temperature from 10° to 38° C., more preferably from 25° to 35° C. During the cultivation, pH of culture fluid is controlled within a range of 5.0 to 7.0, more preferably 6.0 to 7.0. When an ordinary fermentor is employed for the cultivation, it is operated under those conditions as involving aeration at a rate of 1/10 to 1 vvm and agitation at a rate of 100 to 600 rpm. The cultivation is completed within a time ranged from 16 to 80 hours. After the completion of cultivation, the culture fluid is cooled, and centrifuged to harvest the bacterial cells in a slurry of precipitate.

For immobilization of enzyme, one can use any of various existing methods, if applicable. However, only an example is described below. The slurry is mixed with a solution of sodium alginate into a uniform cell suspension, which is then dropped in a form of small drops into a stirred solution of calcium chloride to solidify in a form of spherical pellets. The pellets are collected, washed with water, and then impregnated with a polyethyleneimine solution. The impregnated pellets are treated with a glutaraldehyde solution to convert into a final preparation of immobilized enzyme.

As a reactor, one can use a jacketed column packed with any of such immobilized enzymes. A 20–60% (w/w) sucrose solution, pH 5.5, is passed through the column maintained at 25° C. The effluent from the column is filtered, deionized with ion exchange resins, and evaporated into a syrup, which is a final product obtained by a method according to the present invention. The ratio of trehalulose:isomaltulose in such a product is in a range from 4:1 to 10:1. If desired, one can process it easily into a much more trehalulose-rich preparation in a higher state of purity through chromatographic fractionations on ion-exchange resin columns.

Depending on the high solubility of trehalulose in water, such high trehalulose syrups as obtained above can be used in a variety of food products, in particular moist goods, to elongate their self-lives in combination with any of such sugars as fructose, isomaltulose, high-fructose corn syrup, maltitol and so forth, in combination with or without any of intense sweeteners.

DESCRIPTION OF THE PREFERRED EMBODIMENTS

In the production of isomaltulose and trehalulose according to the present invention, the use of *Pseudomonas mesoacidophila* MX-45 or *Agrobacterium radiobacter* MX-232 instead of *P. rubrum* and a microorganism of the genus Serratia or Erwinia which have been conventionally used may result in increased production of trehalulose syrups.

The trehalulose syrups obtained by the present invention contain substantially a high amount of trehalulose over isomaltulose. Accordingly, even the resulting product is concentrated, crystalline isomaltulose cannot be separated out, because isomaltulose does not reach the saturating concentration.

Furthermore, since only small amounts of glucose and fructose are formed in the enzymatic conversion of the present invention, color formation of the product during the processing is considerably lower, and a lesscolored final product is obtained through a simplified decoloring treatment. In addition, since the ratio of isomaltulose formation from sucrose is lower in the present process than in the conventional one, crystallization of isomaltulose from the reaction mixture may be avoided. One can, therefore, apply a higher concentration of sucrose solution to the reactor for the purpose of controlling microbial contamination, and further a cost saving in the evaporation process.

The present invention is illustrated by the following nonrestlictive details of examples the inventors have carried out.

EXAMPLE 1

Enzyme production

The medium used here contained 100 g sucrose, 10 g peptone, 3 g meat extract, 5 g yeast extract, 2 g disodium hydrogen phosphate dodecahydrate and 3 g sodium chloride per liter, and adjusted at a pH of 6.5 to 7.0 with 1N sodium hydroxide. All sterilizations were carried out by autoclaving at 120° C. for 20 minutes.

A loopful of a slant culture of *Pseudomonas mesoacidophila* MX-45 was transferred into 100 ml medium in a 500-ml shaking flask, and incubated for 24 hours at 28° C. on a shaker reciprocating at 140 rpm. The culture was then seeded in 3 liter sterilized medium in a 5-liter jar-fermentor. Cultivation was carried out at 28° C. for 60 hours with aeration of $\frac{1}{4}$ vvm and mechanical agitation of 430 rpm. During the cultivation, the culture was automatically controlled at about 6.5 of pH and at a temperature of 28° C.

The culture broth thus obtained had a glucosyltransferase activity of 30 U/ml, where one unit (U) was defined as an amount of enzyme which catalyzed transformation of sucrose in an initial rate of one μ mole/min in a 20% (w/v) sucrose solution in water, pH 5.5, at 20° C.

Immobilization of enzyme

The culture broth was cooled to 5° C. and centrifuged at 8000 G for 5 minutes. The supernatant was discarded, and the precipitate was recovered. The latter was mixed with 4% (w/v) sodium alginate solution in a volume ratio 1:1. The mixture was placed in a dropping equipment with 0.5-mm pore nozzles, and dropped in droplet forms into a stirred solution of 0.25 M calcium chloride to solidify in spherical pellets. After 2-hour aging with occasional stirs, the pelleted enzymes were collected on a filter screen, and washed well with water.

The pelleted enzymes were then immersed for 5 minutes in equivalent of 2% (w/v) polyethyleneimine (PEI) solution previously adjusted to pH 5.5 with hydrochloric acid. The immersed pellets were recovered from the solution on a filter screen, and immediately thrown into a stirred solution of 0.5% (w/v) glutaraldehyde (GA) at 5° C. During 30 minutes of the treatment with continuous stirring, the immobilization of cellular glucosyltransferase was completed. The pellets of immobilized enzyme were collected on a filter screen and washed well with water. The yield of the immobilized enzyme preparation was 200 g in wet weight.

Some characteristics of the preparation was then examined. The glucosyltransferase activity of this preparation was determined to be about 70 U/g. A rapid thermal inactivation of the enzyme preparation was observed at 45° C. or more in an experiment wherein 5 g samples were immersed for up to 18 hours in 90 ml of 0.1 M calcium acetate buffer, pH 5.5, at various temperatures ranged from 25° to 50° C. The preparation was highly active in a pH range of 5.0° to 7.0. It was also found in a comparable reaction experiment at various temperatures ranged from 15° to 30° C. that the trehalulose formation increased as the temperature was lower, and on the contrary that the isomaltulose formation as well as monosaccharide liberation increased as the temperature was higher.

Preparation of trehalulose and isomaltulose

In a column tube of 15 mm in diameter and 300 mm in height, 25 g in wet weight of the immobilized enzyme preparation derived from MX-45 was charged. A 50% (w/w) sucrose solution was passed through the column in a flow rate of 8.5 ml/h at 15°, 25° and 30° C. The effluent was called reaction liquid. The sugar composition of the reaction liquid at each temperature was shown in the following table:

TABLE 1

| | Sugar composition of the reaction liquid (% of the total sugar) | | |
|---|---|---|---|
| | 15° C. | 25° C. | 30° C. |
| Fructose | 0.1 | 0.2 | 0.3 |
| Glucose | 0.1 | 0.2 | 0.3 |
| Sucrose | 1.0 | 1.0 | 1.0 |
| Isomaltulose | 8.7 | 16.2 | 18.0 |
| Trehalulose | 89.7 | 82.0 | 80.0 |
| Other carbohydrates | 0.4 | 0.4 | 0.4 |
| Total | | 100 | |

The liquid was filtered, deionized with cation-and anion-exchange resins, and evaporated under a reduced pressure to a syrup which contained trehalulose as the main component. This high trehalulose syrup was less in monosaccharide, more rich in trehalulose and more transparent when compared with a isomaltulose syrup prepared as a subsidiary product in a conventional crystalline isomaltulose production. That is, the rate of trehalulose and isomaltulose formed being 10.3:1 at 15° C., 5.0:1 at 25° C. and 4.4:1 at 30° C.

EXAMPLE 2

Enzyme Production

To a mixture of 100 g sucrose, 10 g peptone, 1 g meat extract, 2 g disodium hydrogen phosphate and 3 g sodium chloride were added 1 liter of water to obtain a medium, followed by addition of sodium hydroxide solution and then the medium was adjusted to pH 6.5–7.0. The medium was sterilized at a temperature of 120° C. for 20 minutes in an autoclave.

A loopful of a slant culture of *A. radiobacter* MX-232 was inoculated in 100 ml of the medium in a 500 ml-shaking flask, and incubated at 28° C. for 24 hours on a shaker reciprocating at 140 rpm. The culture was then seeded in 3 liter of the sterilized medium in a 5 liter-jar fermentor. Cultivation was carried out at 28° C. for about 48 hours with aeration of $\frac{1}{4}$ and under 460 rpm. During the cultivation, the culture was maintained at 28° C. and the resulting culture broth had a glucosyltransferase activity of 30 U/ml.

Immobilization of Enzyme

The culture broth was cooled to 5° C. and centrifuged at 9,000 G for 10 minutes. The supernatant was discarded to obtain the precipitate which was then mixed with 4% (w/w) of sodium alginate solution in the weight ratio of 1:1. The mixture was placed in the dropping equipment with 0.5 mm-pore nozzles, and dropped in 0.25 M calcium chloride solution to obtain a spherical gel. After 2 hour-aging, the pelleted enzymes thus formed were washed with water.

The pelleted enzymes were then immersed in equivalent of 2% (w/w) polyethyleneimine solution (PEI) previously adjusted to pH 5.5 with HCl for 5 minutes. Immediately after that, the pellets were recovered from the solution on a filter screen, and then thrown into 0.5% glutaraldehyde solution at 5° C. After continuously stirring it for 30 minutes, 300 g of the immobilized enzymes were prepared similarly. The activity thereof was 70 U/g.

Preparation of trehalulose and isomaltulose

In a column tube of 15 mm in diameter and 300 mm in height, the immobilized enzyme preparation from MX-232 was charged. A 50% (w/w) sucrose solution was passed through the column in a flow rate of 8.5 ml/h at 15°, 25° and 30° C. The sugar composition of the reaction liquid at each temperature was shown in the following Table:

TABLE 2

| | Sugar composition of the reaction liquid (% of the total sugar) | | |
|---|---|---|---|
| | 15° | 25° | 30° |
| Fructose | | | |
| Glucose | 0.1 | 0.1 | 0.2 |
| Sucrose | 0.1 | 0.1 | 0.3 |
| Isomaltulose | 1.0 | 1.0 | 1.0 |
| Trehalulose | 89.7 | 83.5 | 80.6 |
| Other carbohydrates | 0 | 0 | 0.2 |
| Total | | 100 | |

The liquid was filtered, deionized with cation-and anion-exchange resins, and evaporated to obtain a syrup containing trehalulose as the main component. The proportional rate of trehalulose and isomaltulose in this high trehalulose syrup was 10.1:1 at 15° C., 5.5:1 at 25° C. and 4.3:1 at 30° C. The transparent syrup was less in monosaccharide, more rich in trehalulose.

The trehalulose syrup according to the present invention has about 50% sweetness as much as sucrose and may enhance in combination with a natural or synthetic high sweetener such as stevia, aspartame, alitame, athesulfam K or sucralose. Simultaneously, it has an effect for improving properties of the high sweetner.

| (Preparation of low cariogenic beverages) | | |
|---|---|---|
| 1 | Formulation of hot cake | |
| | Wheat flour | 200 g |
| | Baking powder | 6 g |
| | Milk | 180 ml |
| | Egg | 50 g |
| | Trehalulose syrup | 80 g |
| | Water | 45 ml |
| | Butter | 10 g |
| 2 | Formulation of strawberry-milk gelly | |
| | Strawberry | 100 g |
| | Milk | 200 ml |
| | Trehalulose syrup | 80 g |
| | Gelatin powder | 7 g |
| | Water | 30 ml |
| | Lemon juice | 5 ml |
| 3 | Formulation of strawberry-containing bavarian cream | |
| | Gelatin powder | 4 g |
| | Water | 6 ml |
| | Milk | 100 ml |
| | Trehalulose syrup | 40 g |
| | Egg yolk | 30 g |
| | Strawberry puree | 70 g |
| | Raw cream | 40 ml |
| 4-1 | Formulation of strawberry jam | |
| | Strawberry | 300 g |
| | Liquid trehalulose | 300 g |
| | Lemon juice | a little |
| 4-2 | Formulation of strawberry jam | |
| | Strawberry | 300 g |
| | Liquid trehalulose | 300 g |
| | Aspartame | 5 g |
| | Lemon juice | a little |

We claim:

1. A biologically pure strain of *Pseudomonas mesoacidophila* MX-45, FERM BP3619, having an activity of converting sucrose into trehalulose and isomaltulose.

2. A biologically pure strain of *Agrobacterium radiobacter* MX-232, FERM BP3620, having an activity of converting sucrose into trehalulose and isomaltulose.

* * * * *